US006870160B1

(12) United States Patent
Daniel

(10) Patent No.: US 6,870,160 B1
(45) Date of Patent: Mar. 22, 2005

(54) METHOD AND APPARATUS FOR MONITORING THE CONDITION OF A LUBRICATING MEDIUM

(75) Inventor: David W. Daniel, Vancouver, WA (US)

(73) Assignee: LSI Logic Corporation, Milpitas, CA (US)

( * ) Notice: Subject to any disclaimer, the term of this patent is extended or adjusted under 35 U.S.C. 154(b) by 190 days.

(21) Appl. No.: 10/293,631

(22) Filed: Nov. 13, 2002

(51) Int. Cl.[7] .............................................. G01N 21/31
(52) U.S. Cl. ..................... 250/301; 250/372; 250/373
(58) Field of Search ................................ 250/301, 372, 250/373

(56) References Cited

U.S. PATENT DOCUMENTS 6,525,345 B1 * 2/2003 Kadota ........................ 257/94
2001/0043327 A1 * 11/2001 Barney et al. ............... 356/326

FOREIGN PATENT DOCUMENTS

DE 10053069 A1 * 5/2002 ........... F01M/11/10

* cited by examiner

Primary Examiner—Constantine Hannaher
(74) Attorney, Agent, or Firm—Barnes & Thornburg

(57) ABSTRACT

An apparatus for monitoring the condition of a lubricating medium includes a UV light source, a UV receiver, a processor electrically coupled to both the UV light source and the UV receiver, and a memory device electrically coupled to the processor. The memory device has stored therein a plurality of instructions which, when executed by the processor, cause the processor to (a) communicate with the UV light source and the UV receiver so as to expose a sample of the lubricating medium to the UV light and generate a UV spectrum of the sample in response thereto, and (b) compare the UV spectrum of the sample to a model spectrum and generate a control signal if the UV spectrum of the sample has a predetermined relationship to the model spectrum.

18 Claims, 4 Drawing Sheets

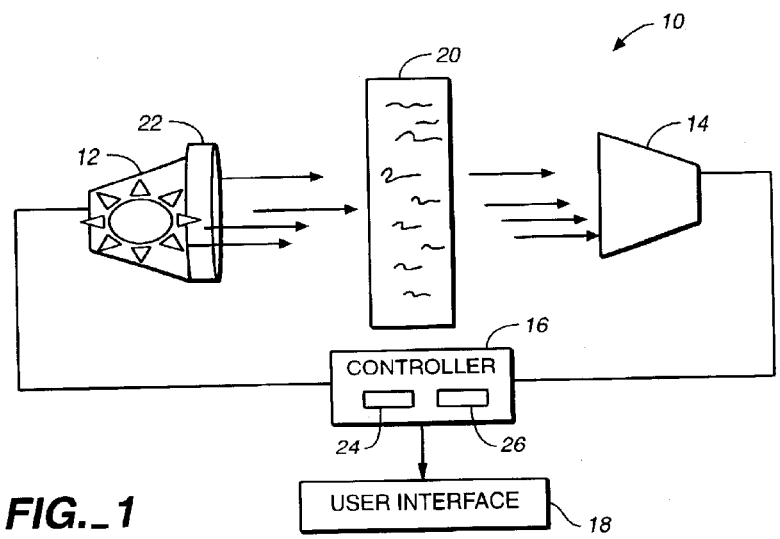
FIG._1
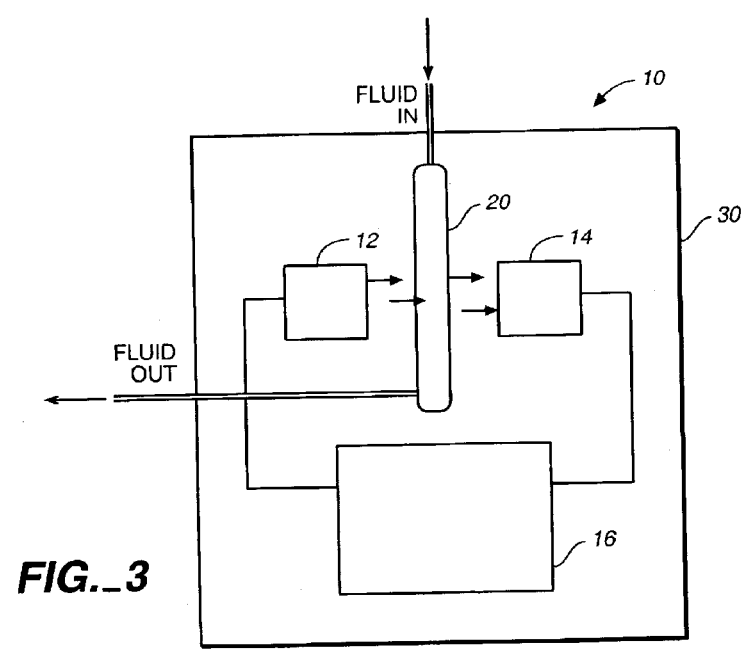
FIG._3

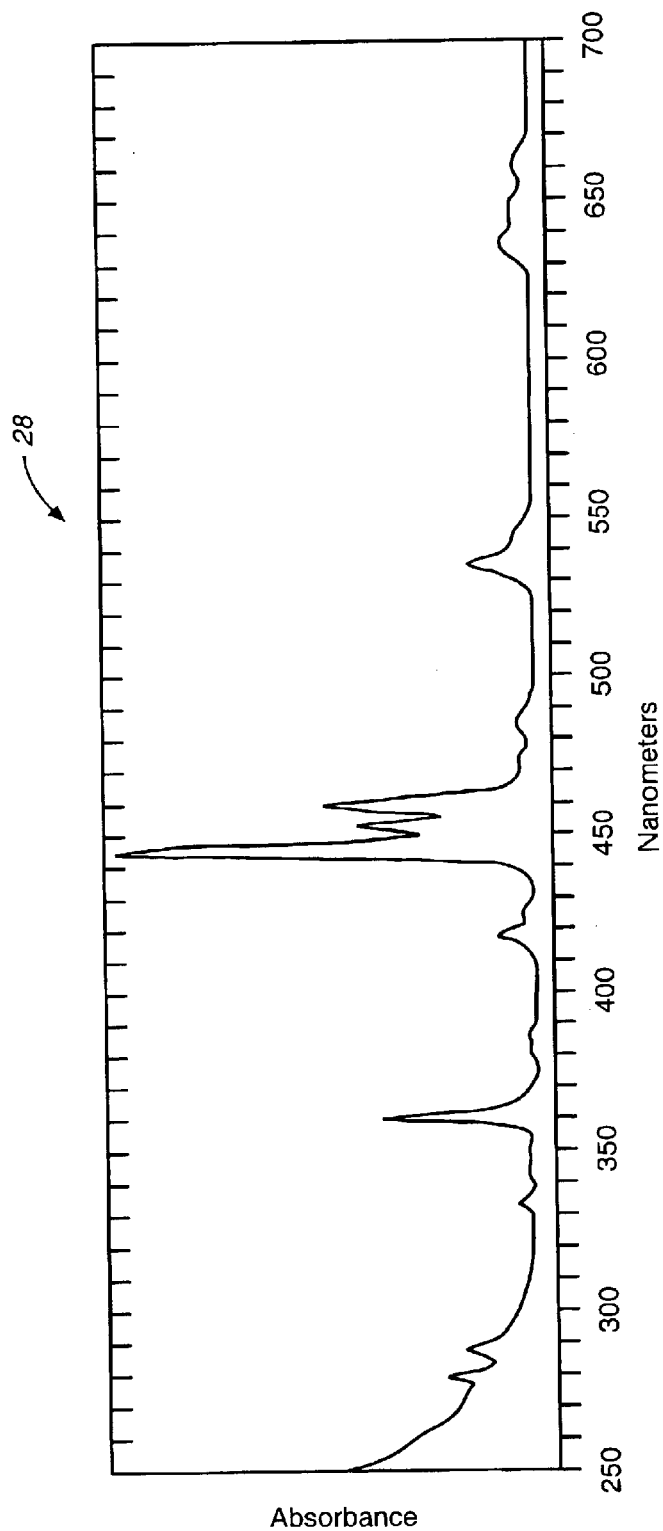
FIG._2

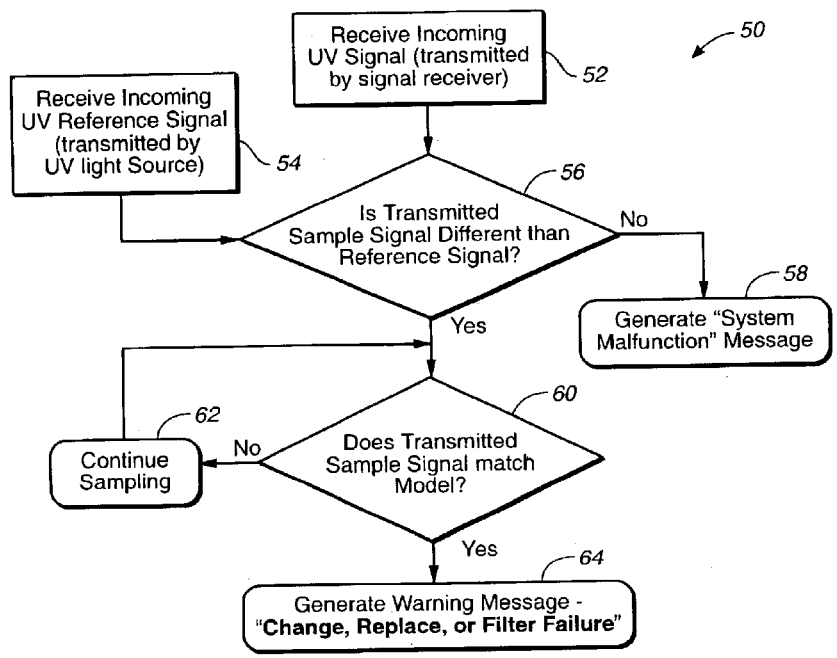
FIG._4

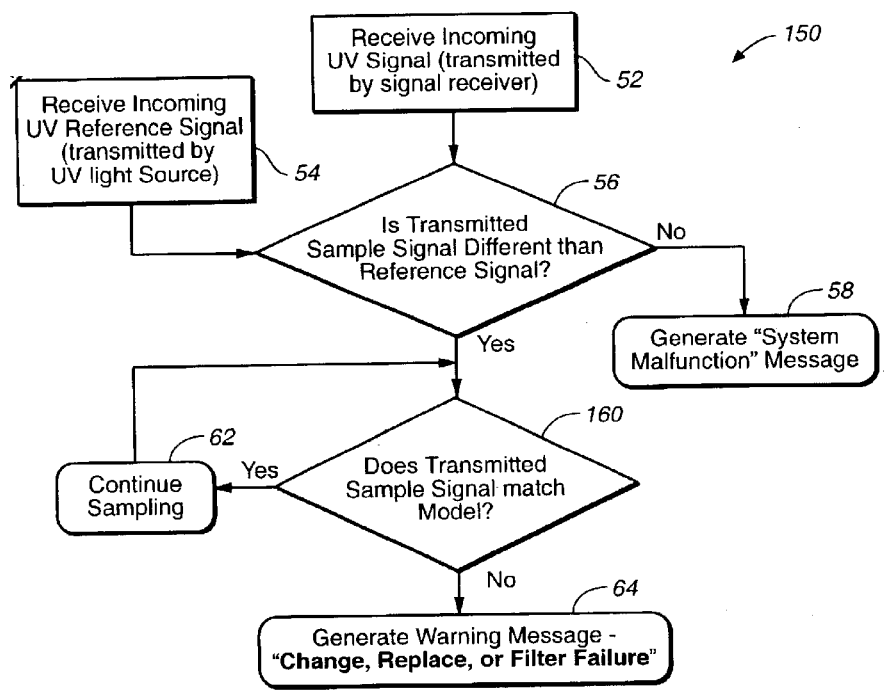
FIG._5

METHOD AND APPARATUS FOR MONITORING THE CONDITION OF A LUBRICATING MEDIUM

TECHNICAL FIELD OF THE DISCLOSURE

The present disclosure relates generally to a lubricating medium, and more particularly to a method and apparatus for monitoring the condition of such a medium.

BACKGROUND OF THE DISCLOSURE

Most friction reducing mediums such as lubricating fluids are embodied as a hydrocarbon based medium having a series of molecular chains which slide across one another. In such a way, the molecular chains act as an interface that separates frictional surfaces thereby reducing heat along with wear and tear of mechanical components.

An inherent problem with such lubricating mediums is the breakdown or chemical decomposition of the material or materials which makeup the fluid. Such breakdown of the lubricating medium may be as a result of decomposition due to heat or mechanical wear. Breakdown may also occur as a result of excessive age of the lubricating medium.

The traditional approach to determining whether a lubricating medium is in need of being replaced involves the monitoring of time intervals. In particular, lubricating mediums are typically replaced as a function of time such as at predetermined time intervals. Such an approach is inexact in nature thereby potentially leading to a number of problems. For example, if the lubricating medium breaks down prematurely, costly damage may occur to mechanical components. On the other hand, the possibility exists for the lubricating medium to be prematurely discarded before the end of its useful life thereby disadvantageously increasing costs.

SUMMARY OF THE DISCLOSURE

In accordance with one aspect of the present disclosure, there is provided a method of monitoring the condition of a lubricating medium. The method includes the step of exposing a sample of the lubricating medium to a UV light source and generating a UV spectrum of the sample in response thereto. The method also includes the step of comparing the UV spectrum of the sample to a model spectrum and generating a control signal if the UV spectrum of the sample has a predetermined relationship to the model spectrum.

In accordance with another aspect of the present disclosure, there is provided an apparatus for monitoring the condition of a lubricating medium. The apparatus includes a UV light source, a UV receiver, a processor electrically coupled to both the UV light source and the UV receiver, and a memory device electrically coupled to the processor. The memory device has stored therein a plurality of instructions which, when executed by the processor, cause the processor to (a) communicate with the UV light source and the UV receiver so as to expose a sample of the lubricating medium to UV light and generate a UV spectrum of the sample in response thereto, and (b) compare the UV spectrum of the sample to a model spectrum and generate a control signal if the UV spectrum of the sample has a predetermined relationship to the model spectrum.

BRIEF DESCRIPTION OF THE DRAWINGS

FIG. 1 is a simplified block diagram of a system for monitoring the condition of a lubricating medium;

FIG. 2 is a graph of a UV spectra of a sample of lubricating medium;

FIG. 3 is a simplified block diagram of the system of FIG. 1 embodied as an assembly mounted on a circuit board; and FIGS. 4 and 5 are process flow charts of control routines executed by the controller of the system of FIG. 1.

DETAILED DESCRIPTION OF THE DISCLOSURE

While the disclosure is susceptible to various modifications and alternative forms, specific embodiments thereof have been shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure as defined by the appended claims.

According to the present disclosure, there is provided an in-situ ultraviolet (UV) monitoring and control system for determining the proper time to change (i.e., replace) a lubricating medium. The systems, apparatus, and methods described herein may be used to monitor the useful life of, for example, automotive crank case oil, pump oil, reciprocating oil, etcetera. As such, the concepts of the present disclosure may be integrated into or otherwise used in the construction of, for example, automotive engines, mechanical pumps, semiconductor process equipment, etcetera.

Referring now to FIG. 1, there is shown one such exemplary system 10. The system 10 includes a UV light source 12 and a UV receiver 14. Both the UV light source 12 and the UV receiver 14 are electrically coupled to a controller 16. As shown in FIG. 1, a user interface 18 such as a display monitor or audible playback device is electrically coupled to the controller 16. A fluid container 20 is positioned between the UV light source 12 and the UV receiver 14. In such a way, lubricating medium positioned in the fluid container 20 may be exposed to UV light from the UV light source 12 with the UV light exiting the container 20 being collected or otherwise received by the UV receiver 14. A quartz filter lens 22 is positioned between the UV light source and the fluid container 20. The filter lens 22 is configured to filter or otherwise select specific wavelengths and frequencies that have a desired absorption for the lubricating medium being sampled or the breakdown components of the medium.

The UV light source 12 may be embodied as any type of UV light source such as a UV emitting laser diode. The UV receiver may be likewise be embodied as any type of UV receiver such as a UV sensitive photodiode array. The controller 16 includes a number of electronic components commonly associated with electronic units which are utilized in the control of electronic systems. For example, the controller 16 may include, amongst other components customarily included in such devices, a processor 24 such as a microprocessor and a memory device 26 such as a programmable read-only memory device ("PROM") including erasable PROM's (EPROM's or EEPROM's). It should be appreciated that the processor and the memory device may be integrated into a common device.

The memory device 26 is configured to store, amongst other things, instructions in the form of, for example, a software routine (or routines) which, when executed by the processor 24, allows the controller 16 to monitor the condition of the lubricating medium in the fluid container 20. To do so, the controller 16 actuates the UV light source 12 thereby exposing the sample of lubricating medium in the fluid container 20 to filtered UV light. The UV receiver 14 then collects or otherwise receives the UV light exiting the sample of lubricating medium in the fluid container 20. As a result, a UV spectrum 28 (see FIG. 2) of the sample of lubricating medium is generated based on the UV light collected from the sample.

The UV spectrum 28 of the sample is then compared to one or more spectrum models to determine the condition of the lubricating medium. For example, the UV spectrum 28 of the sample may be compared to a spectrum model of the same type of lubricating medium subsequent to decomposition thereof. In other words, the UV spectrum 28 of the sample may be compared to a model spectrum of medium of the same type that is predetermined to be in need of replacement or changing. In this case, if the UV spectrum 28 of the sample matches the spectrum model of the decomposed medium, the controller 16 concludes that it is time to change or otherwise replace the lubricating medium from which the sample was taken. What is meant herein by the terms "match" or "matches" is that a given spectrum model is the same as, or within a predetermined tolerance range of, the UV spectrum of the sample of lubricating medium.

Conversely, the UV spectrum 28 of the sample may be compared to a spectrum model of the same type of lubricating prior to decomposition thereof. In other words, the UV spectrum 28 of the sample may be compared to a model spectrum indicative of known "good" sample of the same type of lubricating medium (i.e., medium that is not yet in need of replacement). In this case, if the UV spectrum 28 of the sample does not match the spectrum model of the "good" medium, the controller 16 concludes that it is time to change or otherwise replace the lubricating medium from which the sample was taken.

In addition to the use pre-programmed spectrum models, UV spectrum emissions may be "learned" by the system 10. In particular, the system 10 may be configured to "learn" how the lubricating medium changes with time (depending on the decomposition components and their corresponding spectral absorption toward the ultraviolet). If the medium changes beyond a predetermined level, the controller 16 concludes that the lubricating medium is in need of being replaced.

Referring now to FIG. 3, there is shown the system 10 embodied as an assembly mounted on a circuit board 30. In this case, a complete system 10 is mounted on a circuit board 32. The fluid container 20 is embodied as a quartz tube through which the lubricating medium is pumped or bled off from a separate fluid source. The control algorithm for controlling operation of the system 10 may be a part of the on-chip ROM of the controller 16, which, in this case, is embodied as an ASIC device. The UV light source 12 is embodied as a laser diode that generates and transmits UV light through the quartz tube 20. UV light exiting the quartz tube 20 is received by the UV receiver 14 which is embodied as, for example, a photo diode (UV) array or single UV diode.

As described above, the transmitted UV signal is compared to a pre-programmed reference spectrum model for the lubricating medium of interest. The sampling rate may be set to fit the needs of a given application. In this case, UV spectrum emissions can be learned by the system 10 or pre-programmed models for comparison to the transmitted signal may be utilized. In other words, the onboard system 10 may be configured to "learn" how the lubricating medium changes with time (depending on the decomposition components and their corresponding spectral absorption toward the ultraviolet).

Referring now to FIG. 4, there is shown a flowchart of a control routine 50 which is executed by the controller 16 in conjunction with the use of a spectrum model of a decomposed lubricating medium of interest. The routine 50 commences with step 52 in which the controller 16 receives the output from the UV receiver 14. In particular, a UV spectrum 28 of the sample of lubricating medium in the fluid container 20 is generated in response to exposure of the sample to UV light from the UV light source 12. At the same time, as shown in step 54, the controller 16 samples the UV transmissions from the UV light source 12. In this way, as shown in step 56, the controller 16 may compare the two signals to ensure that the lubricating medium is, in fact, present in the fluid container 20. In particular, if the signal from the receiver 14 is substantially the same as the signal from the light source 12, the controller 16 concludes that either the container 20 is devoid of lubricating medium or the system is otherwise malfunctioning and the routine 50 advances to step 58. In step 58, an error message is generated and provided to the user via the user interface 18. However, if the signal from the receiver 14 differs from the signal from the light source 12, the controller 16 concludes that a valid reading is being received and the routine 50 advances to step 60.

In step 60, the controller 16 compares the UV spectrum 28 from the sample of lubricating medium in the fluid container 20 to a spectrum model of the same type of lubricating medium subsequent to decomposition thereof. In other words, the UV spectrum 28 of the sample is compared to a model spectrum of lubricating medium of the same type that has been determined to be in need of replacement (i.e., changing). If the UV spectrum 28 of the sample does not match the spectrum model of the decomposed medium, the controller 16 concludes that the lubricating medium is not yet in need of changing and the routine advances to step 62 so as to continue sampling the medium. However, if the UV spectrum 28 of the sample matches the spectrum model of the decomposed medium, the controller 16 concludes that it is time to change or otherwise replace the lubricating medium from which the sample was taken, an output signal is generated, and the routine 50 advances to step 64.

In step 64, the controller 64 generates a warning message indicative of the need to change the lubricating medium. Such a warning message may be transmitted to another electronic unit for use by the unit, may be displayed to the user on a display monitor, or may be played back to a user on a playback device, for example. The routine 50 then ends until reactivated.

Referring now to FIG. 5, there is shown a flowchart of a control routine 150 which is executed by the controller 16 in conjunction with the use of a spectrum model of a "good" or otherwise non-decomposed lubricating medium of interest. The routine 150 is somewhat similar to the routine 50. As a result, similar reference numerals are used in FIG. 5 to designate steps which are similar to corresponding steps in FIG. 4. In particular, the routine 152 executes steps 52, 54, 56, and 58 in a similar manner to as described above in regard to FIG. 4.

However, in step 160 of the routine 150, the controller 16 compares the UV spectrum 28 from the sample of lubricating medium in the fluid container 20 to a spectrum model of the same type of lubricating prior to decomposition thereof. In other words, the UV spectrum 28 of the sample may be compared to a model spectrum indicative of known "good" sample of the same type of lubricating medium (i.e., medium that is not yet in need of replacement). If the UV spectrum 28 of the sample matches the spectrum model of the known "good" sample of medium, the controller 16 concludes that the lubricating medium is not yet in need of changing and the routine advances to step 62 so as to continue sampling the medium. However, if the UV spectrum 28 of the sample does not match the spectrum model of the "good" medium, the controller 16 concludes that it is time to change or otherwise replace the lubricating medium from which the sample was taken, an output signal is generated, and the routine 150 advances to step 64.

In step 64, the controller 64 generates a warning message indicative of the need to change the lubricating medium. Such a warning message may be transmitted to another electronic unit for use by the unit, may be displayed to the user on a display monitor, or may be played back to a user on a playback device, for example. The routine 150 then ends until reactivated.

As described herein, the concepts of the present disclosure have numerous advantages. For example, the monitoring methods described herein may be utilized to more accurately identify the need to change a lubricating medium relative to, for example, heretofore utilized time-based approaches.

While the concepts of the present disclosure has been illustrated and described in detail in the drawings and foregoing description, such illustration and description is to be considered as exemplary and not restrictive in character, it being understood that only exemplary embodiments have been shown and described and that all changes and modifications that come within the spirit of the concepts of the present disclosure are desired to be protected.

There are a plurality of advantages of the concepts of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of the apparatus and methods of the present disclosure that incorporate one or more of the features of the present disclosure and fall within the spirit and scope of the invention defined by the appended claims.

What is claimed is:

1. A method of monitoring the condition of a lubricating medium, method comprising the steps of:
   exposing a sample of the lubricating median to a UV light source and generating a UV spectrum of the sample in response thereto; and
   comparing the UV spectrum of the sample to a model spectrum and generating a control signal if the UV spectrum of the sample has a predetermined relationship to the model spectrum.

2. The method of claim 1, wherein the comparing step comprises generating the control signal if the UV spectrum of the sample matches the model spectrum.

3. The method of claim 1, wherein the comparing step comprises generating the control signal if the UV spectrum of the sample does not match the model spectrum.

4. The method of claim 1, further comprising the step of generating a warning message to a user in response to generation of the control signal.

5. The method of claim 4, further comprising the step of displaying the warning message to the user on a display monitor.

6. The method of claim 4, further comprising the step of playing the warning message to the user on an audible playback device.

7. The method of claim 1, wherein the exposing step comprises advancing the sample of lubricating medium between a UV light source and a UV receiver.

8. The method of claim 7, wherein advancing the sample of lubricating medium between a UV light source and a UV receiver comprises advancing the sample between a UV emitting laser diode and UV sensitive photodiode array.

9. An apparatus for monitoring the condition of a lubricating medium, the apparatus comprising:
   a UV light source,
   a UV receiver,
   a processor electrically coupled to both the UV light source and the UV receiver, and
   a memory device electrically coupled to the processor, the memory device having stored therein a plurality of instructions which, when executed by the processor, cause the processor to:
   communicate with the UV light source and the UV receiver so as to expose a sample of the lubricating medium to UV light and generate a UV spectrum of the sample in response thereto, and
   compare the UV spectrum of the sample to the model spectrum and generate a control signal if the UV spectrum of the sample has a predetermined relationship to the model spectrum.

10. The apparatus of claim 9, wherein the plurality of instructions, when executed by the processor, further caused the processor to generate the control signal if the UV spectrum of the sample matches the model spectrum.

11. The apparatus of claim 9, wherein the plurality of instructions, when executed by the processor, further cause the processor to generate the control signal if the UV spectrum of the sample does not match the model spectrum.

12. The apparatus of claim 9, wherein the plurality of instructions, when executed by the processor, further cause the processor to generate a warning message a user in response to generation of the control signal.

13. The apparatus of claim 12, further comprising a display monitor electrically coupled to the processor, wherein the plurality of instructions, when executed by the processor, further cause the processor to display the message to the user on the display monitor.

14. The apparatus of claim 12, further comprising an audible playback device electrically coupled to the processor, wherein the plurality of instructions, when executed by the processor, further cause the processor to play the wing message to the user on the audible playback device.

15. The apparatus of claim 9, further comprising a fluid container positioned between the UV light source and the UV receiver.

16. The apparatus of claim 15, wherein the fluid container comprises a quartz tube.

17. The apparatus of claim 9, wherein:
   the UV light source comprises UV emitting laser diode, and
   the UV receiver comprises a UV sensitive photodiode array.

18. The apparatus of claim 17, further comprising a quartz tube positioned between the UV emitting laser diode and the UV sensitive photodiode array.

* * * * *